United States Patent
Hanaoka et al.

(10) Patent No.: US 7,580,055 B2
(45) Date of Patent: Aug. 25, 2009

(54) DEVICE FOR INSPECTING APPARATUS OF A ROD-LIKE ARTICLE

(75) Inventors: Chihiro Hanaoka, Tokyo (JP); Yasuhiro Otaka, Tokyo (JP); Shinzo Kida, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 1445 days.

(21) Appl. No.: 10/799,696

(22) Filed: Mar. 15, 2004

(65) Prior Publication Data

US 2004/0173226 A1 Sep. 9, 2004

Related U.S. Application Data

(63) Continuation of application No. PCT/JP02/09817, filed on Sep. 25, 2002.

(30) Foreign Application Priority Data

Sep. 25, 2001 (JP) .............................. 2001-291064

(51) Int. Cl.
  *H04N 7/18* (2006.01)
  *H04N 9/47* (2006.01)
(52) U.S. Cl. .................................................. 348/128
(58) Field of Classification Search ........................ None
  See application file for complete search history.

(56) References Cited

U.S. PATENT DOCUMENTS 5,228,462 A * 7/1993 Osmalov et al. ............. 131/280
5,287,524 A * 2/1994 Rizzoli et al. .................. 348/86
5,347,853 A * 9/1994 Hoppe et al. .................... 73/82
5,414,270 A * 5/1995 Henderson et al. ...... 250/559.46
5,432,600 A * 7/1995 Grollimund et al. ....... 356/237.2
5,560,515 A * 10/1996 Dyett et al. .................. 221/135
6,181,372 B1   1/2001 Neri et al.

FOREIGN PATENT DOCUMENTS

| JP | 10-52247 A | 2/1989 |
| JP | 6-160288 A | 6/1994 |
| JP | 2000-093150 A | 4/2000 |
| JP | 2000-348166 A | 12/2000 |

* cited by examiner

*Primary Examiner*—Nhon T Diep
(74) *Attorney, Agent, or Firm*—Birch, Stewart, Kolasch & Birch, LLP

(57) ABSTRACT

An appearance inspection device for a rod-like article comprises a rotatable main drum (20) interposed as a feeding drum in a drum train that defines a feeding path in a filter cigarette manufacturing machine, upstream and downstream bypass drum trains (24, 40) located in the outside of the main drum (20) and receiving a filter cigarette (FC) from the main drum (20) to bypass the cigarette, and an inspection camera (42) situated between the bypass drum trains (24, 40) in a circumferential direction of the main drum (20). The inspection camera (42) directly or indirectly images exposed circumferential surfaces of filter cigarettes (FC), that are different from one another, when the filter cigarettes (FC) are conveyed on the main drum (20) and each of the bypass drum trains (24, 40).

8 Claims, 3 Drawing Sheets

DEVELOPMENT VIEW OF
CIGARETTE OUTER SURFACE

DEVICE FOR INSPECTING APPARATUS OF A ROD-LIKE ARTICLE

This application is a Continuation of co-pending PCT International Application No. PCT/JP02/09817 filed on Sept. 25, 2002, which designated the United States, and on which priority is claimed under 35 U.S.C. § 120, and which claims priority under 35 U.S.C. § 119(a) on Patent Application No(s). 2001-291064 filed in Japan on Sept. 25, 2001, the entire contents of which are hereby incorporated by reference.

TECHNICAL FIELD

The present invention relates to an appearance inspection device for detecting defects, such as dirt, stains and the like, on the outer surface of a cigarette or filter cigarette as a rod-like article.

BACKGROUND ART

A filter cigarette-manufacturing machine includes a feeding path for feeding cigarette rods sideways. In other words, cigarette rods are fed in the perpendicular direction relative to their axis. In the cigarette rod-feeding process, a cigarette rod is first cut into equal parts to form two cigarettes. Thereafter, a space is secured between the two cigarettes to dispose a filter plug therein, and then the cigarettes are then in closely contact with both ends of the filter plug to form a cigarette/plug assembly.

Subsequently, the cigarette/plug assembly is wound with a tip paper piece to be formed into a double filter cigarette. The double filter cigarette is then cut into equal parts, thereby obtaining discrete filter cigarettes.

A filter cigarette having an outer surface with any defect in appearance, such as dirt, stain and the like, is a defective product. The defective product must be ejected from the feeding path.

To eject defective products from the feeding path, it is required to detect defects in appearance of products as rod-like articles, namely cigarettes or filter cigarettes, in the feeding process thereof. Generally, the detection is performed by using an inspection camera for imaging the outer peripheral surface of a rod-like article.

With respect to the rod-like article on the feeding path, however, what the inspection camera can image is only a part of the outer peripheral surface of the rod-like article, the part facing the inspection camera. Therefore, imaging the whole area of the outer peripheral surface of the rod-like article requires a plurality of inspection cameras.

More specifically, the feeding path is generally defined by a drum train including a plurality of fluted drums ranged in the feeding path. Rod-like articles on the drum train are conveyed while being sequentially transferred from a fluted drum to the adjacent fluted drum. Accordingly, every time the rod-like article is transferred to the next fluted drum, a different part of the outer peripheral surface of the rod-like article is brought to face outward in a radial direction of the fluted drum. If a plurality of inspection cameras are located in proper positions on the feeding path, these inspection cameras can image different parts of the outer peripheral surface of the rod-like article one after another. As a result, the image of the entire outer peripheral surface of the rod-like article can be obtained by collecting image data from each inspection camera.

It is not easy, however, to secure locating spaces for a plurality of inspection cameras in the feeding path. Moreover, the use of a plurality of inspection cameras raises the cost of an appearance inspection device.

On the other hand, in the feeding process of rod-like articles, if a rod-like article is rotated around its axis when passing the visual field of an inspection camera, it is possible for one inspection camera to image the entire outer peripheral surface of the rod-like article. However, the speed of feeding cigarettes or filter cigarettes on the feeding path is extremely high, so that it is impossible to rotate the rod-article at 360° in a short interval where the rod-like article passes the visual field of the inspection camera.

DISCLOSURE OF THE INVENTION

An object of the present invention is to provide an appearance inspection device for rod-like articles, that is capable of collecting image data of the entire outer peripheral surface of each rod-like article by using only one inspection camera in a feeding process of rod-like articles.

An appearance inspection device of the present invention for achieving the above object comprises a main feeding path, a bypass-feeding path and imaging means. The main feeding path feeds a rod-like article with a first zone of the outer peripheral surface of the rod-like article exposed. The main feeding path has first and second feeding phases that are different from each other with respect to the feeding of the rod-like article and is capable of receiving the rod-like article in the first feeding phase.

The bypass-feeding path receives the rod-like article of the first feeding phase from the main feeding path to then convey the rod-like article and then returns the rod-like article onto the main feeding path so that the rod-like article is conveyed in the second feeding phase. The bypass-feeding path feeds the rod-like article with the second zone thereof exposed, the second zone being a different zone on the outer peripheral surface of the rod-like article from the first zone. The first and second zones cover the entire outer peripheral surface of the rod-like article.

The imaging means includes one inspection camera for directly or indirectly imaging the first and second zones of the rod-like article in the process of feeding the rod-like article on the main and bypass-feeding paths to collect an image data of the entire outer peripheral surface of each rod-like article.

According to the above-described appearance inspection device, the inspection camera images the first and second zones of a rod-like article one after the other in the process of feeding the rod-like article on the main and bypass-feeding paths, thereby being capable of collecting the image data of the entire outer peripheral surface of the rod-like article. Accordingly, it is possible to detect defects in appearance, such as dirt, stains and the like, of the rod-like article on the basis of the image data.

As described above, the image data of the entire outer peripheral surface of the rod-like article can be obtained by using a single inspection camera. Thus, the inspection camera location is easy, and the structure of the entire appearance inspection device is simple, which makes it possible to provide the appearance inspection device at a low cost.

It is preferable that the inspection camera be so located as to directly image the first zone of a target rod-like article on the main feeding path, and that the imaging means further include a plurality of reflecting members for providing reflected images of the second zone of the target rod-like article to the inspection camera when the target rod-like article is conveyed on the bypass-feeding path. Specifically, what the reflecting members provide for the inspection camera are the reflected images of two parts obtained by subdividing the second zone.

Since reflecting mirrors or prisms as such reflecting members can use, it is possible to easily obtain an optical system between the inspection camera and the bypass-feeding path.

Furthermore, the inspection camera is capable of simultaneously imaging the first zone of one rod-like article on the main feeding path and the second zone of another rod-like article on the bypass-feeding path. In this case, the inspection camera can obtain the image data corresponding to the entire outer peripheral surface of a single rod-like article through one imaging action, thereby being capable of securely obtaining the image data of the entire outer peripheral surface of the rod-like article even if the speed of feeding rod-like articles is increased.

Specifically, the bypass-feeding path receives the rod-like article from a bypass position of the main feeding path to convey the rod-like article thereon and then returns the rod-like article to the main feeding path at a returning position located downstream from the bypass position. In this case, length required for the main feeding path is shortened, which makes the appearance inspection device compact.

The appearance inspection device may further include a downstream bypass-feeding path situated downstream from the above-mentioned bypass-feeding path on the main feeding path. In this case, the inspection camera is disposed to face the main feeding path extending between the bypass position for the upstream bypass-feeding path and the returning position for the downstream bypass-feeding path, and directly images the first zone of the target rod-like article on the main feeding path. The imaging means may further include a first reflecting member for providing a reflected image of a part of the second zone of the target rod-like article to the inspection camera when the target rod-like article is conveyed on the upstream bypass-feeding path and a second reflecting member for providing a reflected image of the rest of the second zone of the target rod-like article to the inspection camera when the target rod-like article is carried on the downstream bypass-feeding path.

It is preferable that the inspection camera simultaneously image the first zone of one rod-like article on the main feeding path, the above-mentioned part of the second zone of another rod-like article on the upstream bypass-feeding path, and the rest of the second zone of further another rod-like article on the downstream bypass-feeding path.

The main feeding path includes a rotatable main drum and a plurality of feeding flutes provided on the outer peripheral surface of the main drum. The feeding flutes are arranged at regular intervals in a circumferential direction of the main drum. When the main drum rotates, the feeding flutes are classified into every other receiving flutes of the first feeding phase for receiving rod-like articles at a receiving position and other receiving flutes of the second feeding phase. The bypass-feeding path includes a bypass drum train situated near the main drum. The bypass drum train has a plurality of fluted drums for receiving the rod-like article from a receiving flute of the first feeding phase of the main drum to convey the rod-like article thereon and then returning the rod-like article to a receiving flute of the second feeding phase of the main drum.

Since the main drum and the bypass drum train can be easily incorporated into a feeding drum train provided for a filter cigarette-manufacturing machine, the appearance inspection device of the present invention is suitable to a cigarette or filter cigarette appearance inspection.

BEST MODE OF CARRYING OUT THE INVENTION

Figure 1:
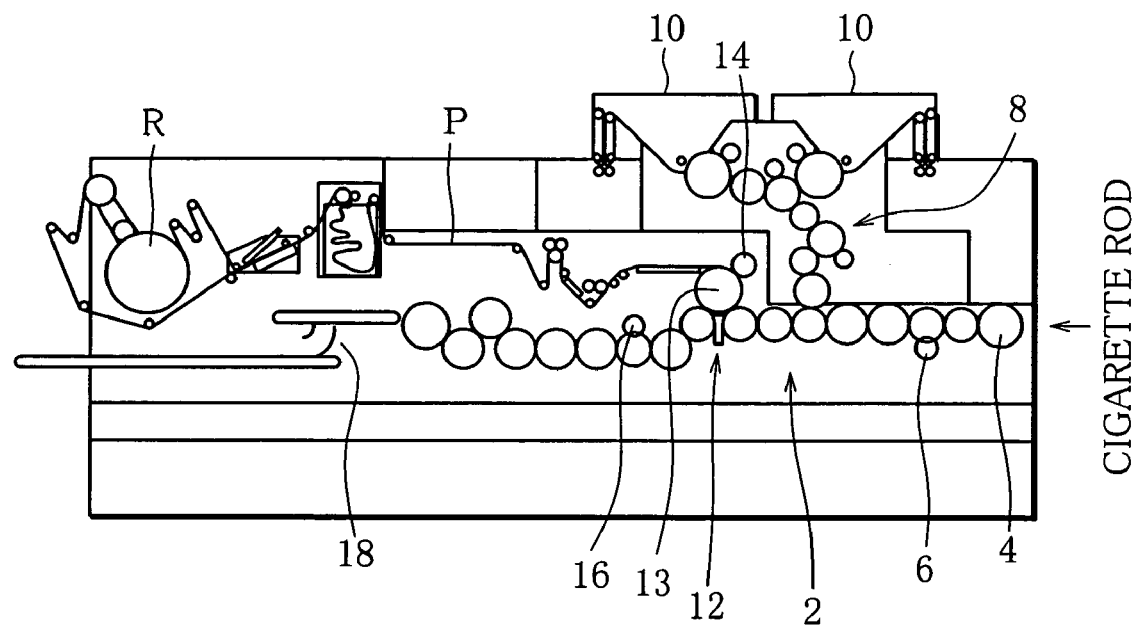
FIG. 1 is a schematic view showing a filter cigarette-manufacturing machine.

A filter cigarette-manufacturing machine in FIG. 1 comprises a drum train 2 that defines a feeding path and extends in a horizontal direction. The drum train 2 includes many feeding drums arranged adjacently to one another. Two adjacent feeding drums are rotated in a reverse direction to each other. Each feeding drum is a fluted drum having a plurality of feeding flutes on an outer peripheral surface thereof, and these feeding flutes are arranged at regular intervals in a circumferential direction of the feeding drum.

Referring to FIG. 1, the feeding drum situated on the right end of the drum train 2 is a receiving drum 4. The receiving drum 4 has feeding flutes each capable of receiving cigarette rods CR one by one while the receiving drum 4 rotates. The cigarette rods CR are intermittently supplied from a cigarette-manufacturing machine (not shown). Thereafter, the cigarette rods CR on the receiving drum 4 are conveyed while being sequentially transferred to the adjacent feeding drum by the rotation of each feeding drum of the drum train 2.

More specifically, the feeding flutes of each feeding drum have suction holes in bottoms thereof, and the suction holes are supplied with suction pressures. Accordingly, rod-like articles, such as cigarette rods CR, the after-mentioned cigarettes C, filter plugs FP, double filter cigarettes DFC, filter cigarettes FC, and the like, are conveyed while being sucked within the feeding flutes. Moreover, the transfer of a rod-like article can be done by controlling the suction pressures of feeding flutes of adjacent feeding drums when the feeding flutes of the feeding drums meet each other.

In the process of feeding a cigarette rod CR, the cigarette rod CR is first cut into equal parts to be divided into two cigarettes C. The cutting herein is carried out on the feeding drum having a rotary knife 6. Thereafter, the two cigarettes C are so moved as to separate from each other in axial directions thereof, which secures a predetermined space between the cigarettes C. The space is supplied with a filter plug FP, and the filter plug FP is positioned between the two cigarettes C.

Filter plugs FP are obtained by cutting a filter rod into pieces of a predetermined length. More specifically, filter rods are each stored in a pair of hoppers 10 located above the drum train 2. A drum train 8 extends from the hoppers 10 toward the drum train 2 and includes many fluted drums like the drum train 2, the fluted drums being situated adjacently to one another.

The drum train 8 takes out a filter rod from each hopper 10 and feeds these filter rods toward the drum train 2. In this feeding process, the filter rods are cut into discrete filter plugs FP, and the filter plugs FP are subjected to an alignment process to form a flow of the filter plugs FP in a line. Thus, the filter plugs FP are supplied from a terminal end of the drum train 8 to the space between the two cigarettes C on the drum train 2. Thereafter, each of the two cigarettes C is in closely contact with each end of the filter plug FP to form a cigarette/plug assembly on the drum train 2.

Furthermore, the drum train 2 comprises a rolling section 12 located downstream from the terminal end of the drum train 8. Just before entering the rolling section 12, the cigarette/plug assembly is supplied with a tip paper piece T. Paste is beforehand applied to one side of the tip paper piece T, thereby bonding one end edge of the tip paper piece T to the cigarette/plug assembly.

Subsequently, when the cigarette/plug assembly rolls to pass through the rolling section 12, the tip paper piece T is wound around the cigarette/plug assembly. The winding of the tip paper piece T forms a double filter cigarette DFC in which the two cigarettes C and the filter plug FP are connected through the tip paper piece T. The double filter cigarette DFC is conveyed from the rolling section 12.

The tip paper piece T can be obtained by cutting tip paper P. More specifically, the tip paper P is supplied from a tip paper roll R to a receiving drum 13. The receiving drum 13 is situated immediately above the rolling section 12, and the tip paper P is cut by a rotary knife 14 into discrete tip paper pieces T on the receiving drum 13. Before the cutting of the tip paper P, paste has applied to one side thereof.

In the process of feeding the double filter cigarette DFC on the drum train 2 situated downstream from the rolling section 12, the double filter cigarette DFC passes the feeding drum with a rotary knife 16. At this time, the rotary knife 16 cuts the double filter cigarette DFC at the center of the filter plug FP into two equal parts, thereby forming two filter cigarettes FC. Thereafter, in the process of feeding the filter cigarettes FC on the drum train 2, the two filter cigarettes FC are so moved as to separate from each other and supplied to an arrangement conveyor 18. The arrangement conveyor 18 orients the two filter cigarettes FC to same direction and conveys the filter cigarettes FC toward a packing machine (not shown).

Figure 2:
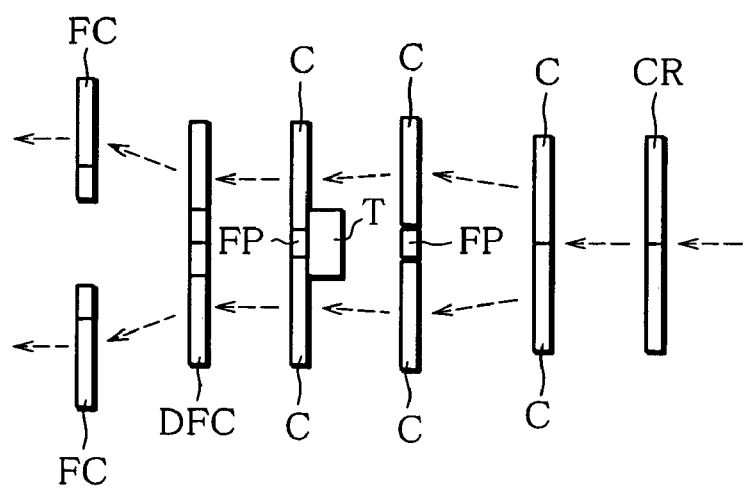
FIG. 2 is a view showing a filter cigarette-manufacturing process carried out by the manufacturing machine in FIG. 1.

FIG. 2 illustrates a process of manufacturing the two filter cigarettes FC out of the above-mentioned cigarette rod CR.

Figure 3:
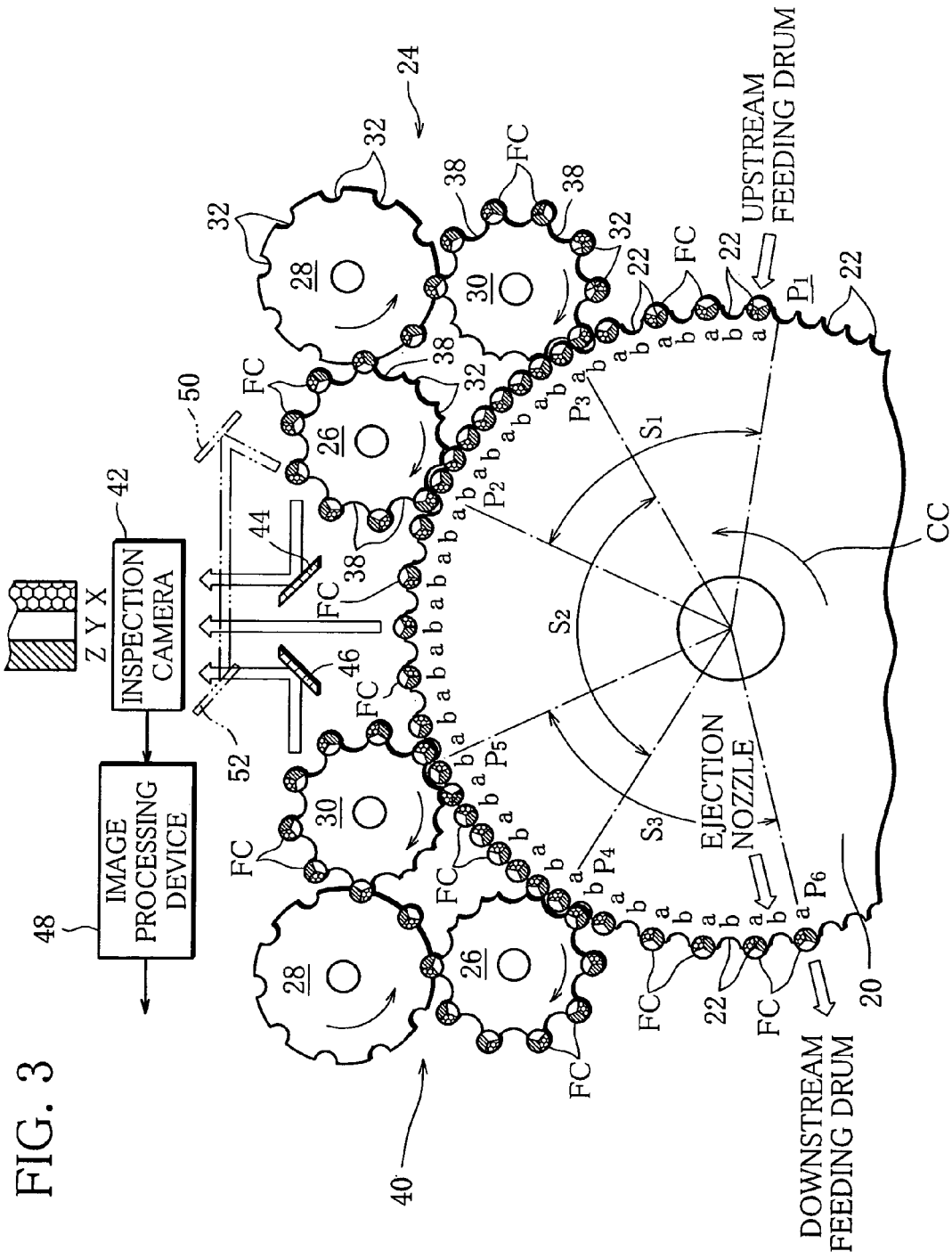
FIG. 3 is a schematic view showing a part of an inspection device incorporated into the manufacturing machine in FIG. 1.

FIG. 3 shows an appearance inspection device incorporated into the aforementioned manufacturing machine.

The appearance inspection device comprises a main drum 20. The main drum 20 may be replaced with one of the feeding drums in the drum train 2, more specifically, a feeding drum located downstream from the feeding drum with the rotary knife 16. The main drum 20 is a fluted drum similar to the feeding drums and has an outer peripheral surface on which a plurality of receiving flutes 22 is formed. The receiving flutes 22 are arranged at regular intervals in a circumferential direction of the main drum 20 and each have a plurality of suction holes in the bottoms thereof.

The feeding drums in the drum train 2 have the same peripheral velocity and the same pitch for the feeding flutes. Accordingly, the adjacent feeding drums are rotated while the feeding flutes thereof meet one another. On the contrary, although the main drum 20 has the same peripheral velocity as the feeding drums, a pitch for the receiving flutes 22 thereof is a half of that for the feeding flutes of the feeding drums. Therefore, the receiving flutes 22 of the main drum 20 alternately meet with the feeding flutes of the adjacent feeding drum.

Figure 4:
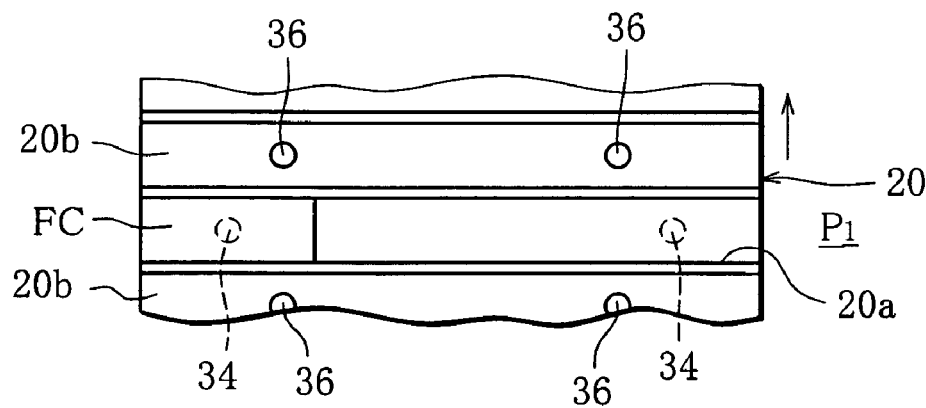
FIG. 4 is a view partially showing an outer peripheral surface of a main drum in FIG. 3.

When the main drum 20 is rotated counterclockwise, that is, in a direction of an arrow CC in FIG. 3, therefore, the receiving flutes 22 of the main drum 20 can alternately receive the filter cigarettes FC from the upstream feeding drum as shown in FIG. 4. The filter cigarette FC received in the receiving flute 22 is conveyed toward the downstream feeding drum. The outer peripheral surface of the main drum 20 or the receiving flutes 22, which are serially arranged in the circumferential direction of the main drum 20, define a main feeding path for the filter cigarettes FC.

In FIG. 4, among the receiving flutes 22 of the main drum 20, the receiving flutes 22 that are capable of receiving the filter cigarettes FC from the upstream feeding drum are each provided with an identification sign "a", whereas the receiving flutes 22 except the receiving flutes 22*a*, or empty receiving flutes 22, are each provided with an identification sign "b".

As is obvious from FIG. 4, when the filter cigarette FC is received by the receiving flute 22*a*, about half circumferential portion of the outer peripheral surface of the filter cigarette FC is covered with the receiving flute 22*a*, while the other half circumferential portion faces outward in a radial direction of the main drum 20 and is exposed outside.

As is clear from the aforementioned, the main drum 20 receives two filter cigarettes FC from the upstream feeding drum at the same time with the receiving flutes 22*a*. To avoid a complicated description, however, the following explanation is provided with a focus on one of the two filter cigarettes FC.

The main drum 20 comprises a bypass drum train 24 in the vicinity of the outer peripheral surface thereof. The bypass drum train 24 is situated downstream from the aforementioned upstream feeding drum in a rotating direction of the main drum 20. The bypass drum train 24 includes, for example, three bypass drums 26, 28 and 30. The bypass drums 26 and 30 are so located as to make rolling contact with the outer circumference of the main drum 20 while rotating, and separated from each other in the rotating direction of the main drum 20. More specifically, the bypass drum 26 is disposed downstream from the bypass drum 30 in the rotating direction of the main drum 26. On the other hand, the bypass drum 28 is so located as to make rolling contact with both the bypass drums 26 and 30 while rotating on the outside of the bypass drums 26 and 30.

The bypass drums 26 through 30 are also fluted drums, and each bypass drum has a plurality of bypass flutes 32 on an outer peripheral surface thereof. The bypass flutes 32 of each bypass drum are disposed at regular intervals in a circumferential direction of the bypass drum and each have a plurality of suction holes on the bottom thereof. The pitch for the bypass flutes 32 of each bypass drum is double the pitch for the receiving flutes 22*a* of the main drum 20, and the bypass drums 26 through 30 have the same peripheral velocity as the main drum 20. Moreover, the bypass drums 26 and 30 are rotated in a reverse direction to the rotating direction of the main drum 20. Accordingly, each bypass flute 32 of the roundabout drum 26 periodically meets with a receiving flute 22*a* of the main drum 20, whereas each bypass flute 32 of the bypass drum 30 meets with a receiving flute 22*b* of the main drum 20.

The bypass drum 28 is rotated in the same direction as the rotating direction of the main drum 20, or in the counterclockwise direction. Therefore, each bypass flute 32 of the bypass drum 28 periodically meets with bypass flutes 32 of the bypass drums 26 and 30, respectively.

As mentioned above, the receiving flutes 22*a* of the main drum 20 receive the filter cigarettes FC from the upstream feeding drum. The filter cigarettes FC in the receiving flutes 22*a* are conveyed along the rotation of the main drum 20 to reach the upstream bypass drum 30. At this time, the bypass flutes 32 of the bypass drum 30 do not meet with the receiving flutes 22*a* of the main drum 20, so that the filter cigarettes FC in the receiving flutes 22a pass the bypass drum 30 and are further conveyed toward the downstream bypass drum 26.

When a filter cigarette FC reaches the bypass drum 26, the receiving flute 22a containing the filter cigarette FC meets with the bypass flute 32 of the bypass drum 26. Then, the filter cigarette FC is transferred from the receiving flute 22a to the bypass flute 32 of the bypass drum 26.

Thereafter, the filter cigarette FC is transferred from the bypass drum 26 through the bypass drum 28 to the bypass drum 30 and received in the bypass flute 32 of the bypass drum 30. The filter cigarette FC on the bypass drum 30 is conveyed toward the outer peripheral surface of the main drum 20.

When the bypass flute 32, in which the filter cigarette FC has been received, meets with the receiving flute 22b of the main drum 20, the filter cigarette FC is transferred from the bypass drum 30 to the receiving flute 22b of the main drum 20 and then are conveyed again on the main drum 20, that is, the main feeding path. Therefore, as illustrated in FIG. 3, on the main drum 20, all receiving flutes 22 located between the bypass drums 26 and 30 receive a filter cigarette FC.

Thereafter, the receiving flutes 22b of the main drum 20 do not meet with the bypass flutes 32 of the bypass drum 26. Therefore, even the filter cigarette FC in the receiving flute 22b reaches the bypass drum 26 again, the filter rod FC is not transferred to the bypass drum 26 and passes the bypass drum 26. As is clear from FIG. 3, after passing the bypass drum train 24, the filter cigarettes FC are all conveyed with received in the receiving flutes 22b of the main drum 20.

In other words, the receiving flutes 22a of the main drum 20 can feed the filter cigarettes FC in a bypass phase that allows the filter cigarettes FC to be transferred to the bypass drum 26. On the contrary, the receiving flutes 22b of the main drum 20 can feed the filter cigarettes FC in a passing phase that allows the filter cigarettes FC to pass the bypass drum 26.

In order to make it possible to securely transfer the filter cigarettes FC between the main drum 20 and the bypass drum train 24, the receiving flutes 22a of the main drum 20 can be supplied with suction pressures through the suction holes thereof when being in a suction zone $S_1$ as shown in FIG. 3, whereas the receiving flutes 22b of the main drum 20 can be supplied with suction pressures through the suction holes thereof when being in a suction zone $S_2$ as shown in FIG. 3.

More specifically, as is apparent from FIG. 3, in view of the circumferential direction of the main drum 20, when $P_1$ denotes a position where the main drum 20 is supplied with the filter cigarettes FC from the upstream feeding drum, and $P_2$ denotes a position where the filter cigarettes FC are transferred from the main drum 20 to the bypass drum 26 to make a detour, the suction zone $S_1$ extends from the immediate before the receiving position $P_1$ to the immediate before the bypass position $P_2$ in the circumferential direction of the main drum 20.

Moreover, when $P_3$ denotes a position where the filter cigarettes FC return from the bypass drum 30 to the main drum 20, and $P_4$ denotes an after-mentioned bypass position, the suction zone $S_2$ extends from the immediate before the returning position $P_3$ to the immediate before the bypass position $P_4$ in the circumferential direction of the main drum 20.

As illustrated in FIG. 4, each receiving flute 22 has a pair of suction holes, for example. The suction holes 34 of the receiving flute 22a and the suction holes 36 of the receiving flute 22b are disposed in different positions from each other in the axial direction of the receiving flute 22. Accordingly, when passing the suction zone $S_1$ while the main drum 20 rotates, the suction holes 34 are connected to a suction slot (not shown) that defines the suction zone $S_1$. On the other hand, the suction holes 36 are connected to a suction slot (not shown) that defines the suction zone $S_2$ when passing the suction zone $S_2$. In addition, these suction slots are formed in a fixed sleeve (not shown). The fixed sleeve is arranged concentrically and unrotatably in the main drum 20.

Furthermore, when the filter cigarette FC is received in the bypass flute 32 of the bypass drum 26 from the receiving flute 22a of the main drum 20, the bypass flute 32 sucks a part of an exposed circumferential surface of the filter cigarette FC. Thus, when the filter cigarette FC is conveyed on the bypass drum 26, part of the outer peripheral surface of the filter cigarette FC, that is hidden in the receiving flute 22a, is so exposed as to face outward in a radial direction of the bypass drum 26.

When the filter cigarette FC is conveyed on the bypass drum 26, the exposed circumferential surface of the filter cigarette FC should be widely secured. To this end, the bypass flute 32 of the bypass drum 26 has smaller depth than the receiving flute 22, as is obvious from FIG. 3.

On the other hand, the bypass flute 32 of the bypass drum 28 has the same depth as the receiving flute 22. Therefore, when the filter cigarette FC is transferred from the bypass drum 26 to the bypass drum 28, the exposed part of the outer peripheral surfaces of the filter cigarette FC on the bypass drum 28 and that of the filter cigarette FC in the receiving flute 22a are same.

Furthermore, the bypass flute 32 of the bypass drum 30 has the same depth as the bypass flute 32 of the bypass drum 26. Accordingly, the filter cigarettes FC on the bypass drums 26 and 30 are exposed in the same parts of the outer peripheral surfaces thereof. When the filter cigarette FC is returned to the receiving flute 22b, the filter cigarettes FC in the receiving flutes 22a and 22b are exposed in the same parts of the outer peripheral surfaces thereof.

Furthermore, the bypass drums 26 and 30 have recesses 38 between the bypass flutes 32. When the filter cigarette FC is transferred from the main drum 20 to the bypass drum 26, or when the filter cigarette FC is returned from the bypass drum 30 to the main drum 20, the recesses 38 prevent the filter cigarette FC on the main drum 20 from interfering with the filter cigarette FC on the bypass drum 26 or 30. As a result, it becomes possible to surely carry out the transfer of the filter cigarette FC from the main drum 20 to the bypass drum 26 and the return of the filter cigarette FC from the bypass drum 30 to the main drum 20.

The main drum 20 further comprises a bypass drum train 40 similar to the above-described bypass drum train 24. The bypass drum train 40 is situated downstream from the bypass drum train 24 in the rotating direction of the main drum 20. There is secured a predetermined space between the upstream and downstream bypass drum trains 24 and 40 in the circumferential direction of the main drum 20.

The downstream bypass drum train 40 has the same structure as the upstream bypass drum train 24. Therefore, in the following explanation about the bypass drum train 40, members and portions of the bypass drum train 40 that have the same functions as those of the upstream bypass drum train 24 are referred to by the same reference numerals. Explanations about such members and portions will be omitted, and only distinctive features over the bypass drum train 24 will be described.

The bypass drum 26 of the downstream bypass drum train 40 receives the filter cigarette FC from the receiving flute 22b of the main drum 20 and conveys the received filter cigarette FC. The bypass drum 30 of the bypass drum train 40 returns the filter cigarette FC to the receiving flute 22a of the main drum 20. Accordingly, as for the bypass drum train 40, the receiving flute 22b of the main drum 20 feeds the filter cigarette FC in the bypass phase, while the receiving flute 22a in the passing phase. In consequence, as is apparent from FIG. 3, the filter cigarettes FC that have passed the bypass drum train 40 are all received by the receiving flutes 22a of the main drum 20 and conveyed on the main drum 20.

The above-mentioned bypass position $P_4$ denotes a position where the filter cigarette FC is transferred from the main drum 20 to the bypass drum 26 of the bypass drum train 40. The main drum 20 further includes a suction zone $S_3$. The suction zone $S_3$ supplies a suction pressure to the suction holes 34 of the receiving flute 22a in the same manner as the suction zone $S_1$.

More specifically, when $P_5$ denotes a position where the filter cigarette FC is returned from the bypass drum 30 of the bypass drum train 40 to the main drum 20, and $P_6$ denotes a position where the filter cigarette FC is transferred from the main drum 20 to the downstream feeding drum, the suction zone $S_3$ extends from the immediate after the returning position $P_5$ to the immediate before the delivering position $P_6$ in the circumferential direction of the main drum 20.

Consequently, the filter cigarettes FC received by the receiving flutes 22a at the receiving position $P_1$ of the main drum 20 are deviously conveyed on the upstream and downstream bypass drum trains 24 and 40 in turn, in the process of being conveyed on the main drum 20, and then transferred from the receiving flutes 22a to the downstream feeding drum at the delivering position $P_6$ of the main drum 20.

There is disposed an inspection camera 42 in the outside of the main drum 20. The inspection camera 42 is located between the upstream bypass drum train 24 and the downstream bypass drum train 40 in the rotating direction of the main drum 20 and directed to the outer peripheral surface of the main drum 20. The inspection camera 42 includes a CCD (charge coupled device) and has a predetermined visual field. The visual field of the inspection camera 42 is longer than the length of the filter cigarette FC in respect of the axial direction of the main drum 20 and longer than the whole peripheral length of the filter cigarette FC in respect of the circumferential direction of the main drum 20.

Figure 5:
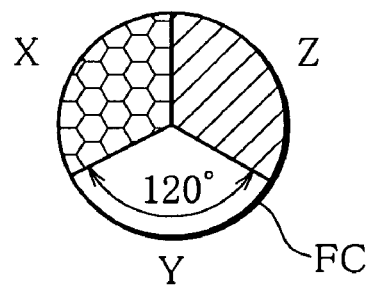
FIG. 5 is a view showing zones of a filter cigarette imaged by an inspection camera in FIG. 3.

When the filter cigarette FC on the main drum 20 passes under the inspection camera 42 while the main drum 20 rotates, the inspection camera 42 directly images part of the outer peripheral surface of the filter cigarette FC. At this time, the image area of the outer peripheral surface of the filter cigarette FC corresponds to a portion that faces outward in the radial direction of the main drum 20. Specifically, referring to FIG. 5, the image area corresponds to a Y zone of the entire outer peripheral surface of the filter cigarette FC, and the Y zone is defined by a sector having a center angle of at least 120°. The Y zone of each filter cigarette FC illustrated in FIG. 3 is not hatched to agree with the one shown in FIG. 5.

Furthermore, as illustrated in FIG. 3, disposed between the inspection camera 42 and the main drum 20 is a pair of reflecting mirrors 44 and 46. The reflecting mirror 44 is directed to the circumferential surface of the bypass drum 26 of the bypass drum train 24. Therefore, when the filter cigarette FC is conveyed on the bypass drum 26, the reflecting mirror 44 reflects an image of an approximately half of the exposed circumferential surface of the filter cigarette FC, namely an image of an X zone, toward the inspection camera 42, which enables the inspection camera 42 to image the X zone. In FIG. 3, the X zone of each filter cigarette FC is hatched with meshes.

On the other hand, the reflecting mirror 46 is directed to the outer peripheral surface of the bypass drum 30 of the bypass drum train 40. Accordingly, when the filter cigarette FC is conveyed on the bypass drum 30, the reflecting mirror 46 also reflects an image of an approximately half of the exposed circumferential surface of the filter cigarette FC, namely an image of a Z zone, toward the inspection camera 42, and the inspection camera 42 images the Z zone. In FIG. 3, the Z zone of each filter cigarette FC is shown with parallel hatched lines.

The X and Z zones are defined by sectors similarly to the Y zone, and these sectors each have a center angle of at least 120°. Moreover, as is obvious from FIG. 3, the X and Z zones indicate different regions of the exposed circumferential surfaces of the filter cigarettes FC.

Figure 6:
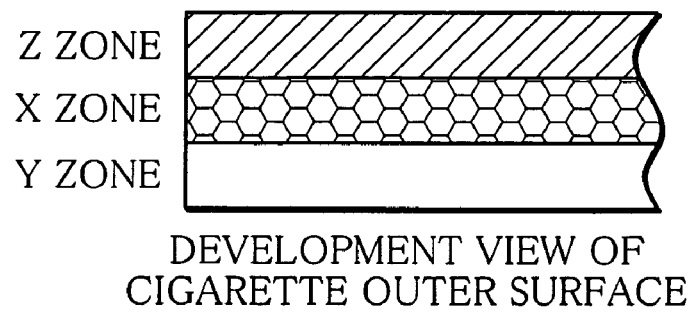
FIG. 6 is a view showing a captured image obtained by the inspection camera.

The inspection camera 42 is capable of performing not only the imaging of the Y zone but also the imaging of the X and Z zones at the same time and obtaining a captured image in which the X, Y and Z zones are pieced together as shown in FIG. 6. As is obvious from the above description, although the X, Y and Z zones in the captured image are obtained from the outer peripheral surfaces of the different filter cigarettes FC, the captured image covers the entire outer peripheral surface of a filter cigarette FC as is clear from FIG. 5 in view of each filter cigarette FC. This means that a single imaging action of the inspection camera 40 can provide a captured image that corresponds to the entire outer peripheral surface of one filter cigarette FC.

The inspection camera 40 sequentially transmits captured images to an image processing device 48. The image processing device 48 collects image data of the entire outer peripheral surface of each filter cigarette FC on the basis of the captured image, and then, based on the image data, decides quality of appearance of each filter cigarette FC.

Specifically, the image transmitted from the inspection camera 40 includes the X, Y and Z zones of the different filter cigarettes FC, so that the image processing device 48 detects defects, such as dirt, stains and the like, from the image data in the captured image, that corresponds to approximately a third part of the outer peripheral surface, respectively, with respect to each filter cigarette FC. In other words, in view of a single filter cigarette FC, substantially thirds of the outer peripheral surface of the filter cigarette FC are sequentially inspected one by one in the feeding process, thus completing the inspection of the entire outer peripheral surface of the filter cigarette FC.

In cases where the image processing device 48 detects a defect in appearance of the filter cigarette FC, the image processing device 48 outputs an ejection signal at a predetermined timing, and then based on the ejection signal, the defective filter cigarette FC is ejected from the main drum 20. More specifically, the main drum 20 has an ejection nozzle (not shown) built-in in the immediate before the delivering position $P_6$. The ejection nozzle blows out ejecting air into the receiving flute 22a through the suction holes 34 based on the ejection signal. The ejecting air blows away defective filter cigarette FC from the receiving flute 22a. In addition, the ejection position of the defective filter cigarettes FC is not limited to the main drum 20 and may be allocated to a feeding drum arranged downstream from the main drum 20.

The present invention is not limited to the aforementioned embodiment and may be modified in various ways.

In the above embodiment, for example, although the reflecting mirrors 44 and 46 are utilized for imaging the X and Z zones of the filter cigarettes FC, these reflecting mirrors may be replaced with prisms or the like.

Furthermore, the filter cigarette FC does not necessarily have to be bypassed from the main drum 20 through the upstream and downstream bypass-feeding drum trains 24 and 40, respectively. For instance, if there are disposed reflecting mirrors 50 and 52 as shown by imaginary lines in FIG. 3, when the filter cigarette FC is conveyed on the upstream bypass-feeding drum train 24, the reflecting mirrors 50 and 52 can simultaneously provide the image of the Z zone of the filter cigarette FC for the inspection camera 42. As a consequence, even if there is provided only one bypass-feeding drum train, the inspection camera 42 is capable of imaging the X, Y and Z zones of the filter cigarettes FC at a time.

The appearance inspection device according to the present invention is capable of inspecting not only the appearance of the filter cigarette FC but also that of the cigarette rod CR, the cigarette C and the double filter cigarette DFC as well. Furthermore, the appearance inspection device may be applied not only to the appearance inspection of tobacco products but also that of various kinds of rod-like articles.

The invention claimed is:

1. An appearance inspection device for a rod-like article comprising:
   a main feeding path for feeding a rod-like article with a first zone of an outer peripheral surface of the rod-like article exposed, said main feeding path having a first and a second feeding phase that are different from each other with respect to feeding of the rod-like article and being capable of receiving the rod-like article in said first feeding phase,
   a bypass-feeding path for receiving the rod-like article in said first feeding phase from said main feeding path to convey the rod-like article and then returning the rod-like article onto said main feeding path so that the rod-like article is fed in said second feeding phase, said bypass-feeding path conveying the rod-like article with a second zone of the outer peripheral surface of the rod-like article exposed, the second zone being different from the first zone, wherein the first and second zones cover the entire outer peripheral surface of the rod-like article, and
   imaging means for collect image data of the entire outer peripheral surface of each rod-like article in a process of feeding the rod-like article on said main and bypass-feeding paths, said imaging means including a single inspection camera for directly or indirectly imaging the first and second zones of the rod-like article.

2. The device according to claim 1, wherein
   the inspection camera is so disposed as to directly image the first zone of a target rod-like article on said main feeding path, and
   the imaging means further includes a plurality of reflecting members for providing a reflected image of the second zone of the target rod-like article for the inspection camera when the target rod-like article is conveyed on said bypass-feeding path.

3. The device according to claim 2, wherein
   the reflecting members provide reflected images of two portions obtained by subdividing the second zone for the inspection camera, respectively.

4. The device according to claim 3, wherein
   the inspection camera simultaneously images the first zone of one rod-like article on said main feeding path and the second zone of another rod-like article on said bypass-feeding path.

5. The device according to claim 1, wherein
   said bypass-feeding path receives the rod-like article from a bypass position of said main feeding path to convey the rod-like article and then returns the rod-like article to said main feeding path at a returning position located downstream from the bypass position.

6. The device according to claim 5, further including a downstream bypass-feeding path situated downstream from said bypass-feeding path on said main feeding path, and
   the inspection camera is located to face said main feeding path extending between the bypass position for said upstream bypass-feeding path and a returning position for said downstream bypass-feeding path and directly images the first zone of a target rod-like article on said main feeding path, wherein
   said imaging means further includes:
   a first reflecting member for providing a reflected image of a part of the second zone of the target rod-like article for the inspection camera when the target rod-like article is conveyed on said upstream bypass-feeding path, and
   a second reflecting member for providing a reflected image of the rest of the second zone of the target rod-like article for the inspection camera when the target rod-like article is conveyed on said downstream bypass-feeding path.

7. The device according to claim 6, wherein
   the inspection camera simultaneously images the first zone of one rod-like article on said main feeding path, the part of the second zone of another rod-like article on said upstream bypass-feeding path, and the rest of the second zone of further another rod-like article on said downstream bypass-feeding path.

8. The device according to claim 1, wherein
   said main feeding path includes:
   a rotatable main drum, and
   a plurality of feeding flutes provided on an outer peripheral surface of the main drum, the feeding flutes being arranged at regular intervals in a circumferential direction of the main drum and being classified into every other receiving flutes of said first feeding phase capable of receiving rod-like articles at a receiving position and the rest of the receiving flutes of said second feeding phase while the main drum rotates, and
   said bypass-feeding path includes:
   a bypass drum train situated in a vicinity of the main drum, the bypass drum train including a plurality of fluted drums for receiving a rod-like article from the receiving flute of said first feeding phase of the main drum to convey the rod-like article and then returning the rod-like article to the receiving flute of said second feeding phase of the main drum.

\* \* \* \* \*